(12) United States Patent
Tu et al.

(10) Patent No.: US 6,406,493 B1
(45) Date of Patent: Jun. 18, 2002

(54) EXPANDABLE ANNULOPLASTY RING AND METHODS OF USE

(76) Inventors: Hosheng Tu, 2151 Palermo, Tustin, CA (US) 92782; Rodolfo C. Quijano, 27451 Lost Trail La., Laguna Hills, CA (US) 92653

(*) Notice: Subject to any disclaimer, the term of this patent is extended or adjusted under 35 U.S.C. 154(b) by 0 days.

(21) Appl. No.: 09/627,523

(22) Filed: Jul. 28, 2000

Related U.S. Application Data

(63) Continuation-in-part of application No. 09/587,135, filed on Jun. 2, 2000.

(51) Int. Cl.[7] ............................. A61F 2/06; A61F 2/24
(52) U.S. Cl. ........................................ 623/2.37
(58) Field of Search ....................... 623/2.36, 2.37, 623/900, 2.14, 2.18, 1.17, 1.15

(56) References Cited

U.S. PATENT DOCUMENTS

| | | | |
|---|---|---|---|
| 4,491,986 A | * 1/1985 | Gabbay | 623/2 |
| 5,163,952 A | 11/1992 | Froix | 623/1 |
| 5,258,020 A | 11/1993 | Froix | 623/1 |
| 5,607,467 A | 3/1997 | Froix | 623/1 |
| 5,855,601 A | * 1/1999 | Bessler et al. | 623/2 |
| 6,077,298 A | 6/2000 | Tu et al. | 623/1.19 |
| 6,224,625 B1 | * 5/2001 | Jayaraman | 623/1.15 |

* cited by examiner

*Primary Examiner*—Bruce Snow

(57) ABSTRACT

An expandable annuloplasty ring which may be enlarged in situ comprising essentially uniform ring distension in the circumferential direction. The expandable annuloplasty ring is usable in pediatric patients whose growth necessitates enlargement of the ring by application of shape-memory material by way of heat activation or other non-mechanical means to accommodate growth of the annulus. The invention includes a non-contact method for post-implantation enlargement of the annuloplasty ring via a magnetic circuit or an external heat source.

6 Claims, 6 Drawing Sheets

EXPANDABLE ANNULOPLASTY RING AND METHODS OF USE

RELATIONSHIP TO COPENDING APPLICATION

This patent application is a continuation-in-part application of application Ser. No. 09/587,135 filed Jun. 2, 2000, the entire contents of which are incorporated herein by reference.

FIELD OF THE INVENTION

The present invention generally relates to improved medical devices and their use. More particularly, the present invention relates to an annular ring or an annuloplasty ring that is timely expandable for correction of certain disorders in the heart valves, blood vessels or other body conduits in a patient.

BACKGROUND OF THE INVENTION

The human's circulatory system consists of a heart and many blood vessels. In its path through the heart, the blood encounters four valves. The valve on the right side that separates the right atrium from the right ventricle has three cusps and is called the tricuspid valve. It closes when the ventricle contracts during a phase known as systole and it opens when the ventricle relaxes, a phase known as diastole. The pulmonary valve separates the right ventricle from the pulmonary artery. The mitral valve, so named because of its resemblance to a bishop's mitre, is in the left ventricle and it separates the left atrium from the ventricle. The fourth valve is the aortic valve that separates the left ventricle from the aorta. In a venous circulatory system, a venous valve is to prevent the venous blood from leaking back into the upstream side so that the venous blood can return to the heart and consequently the lungs for blood oxygenating and waste removing purposes.

In many patients who suffer from diseased or congenitally dysfunctional cardiovascular tissues, a medical implant may be used to correct the problems. A dysfunctional heart valve hinders the normal functioning of the atrioventricular orifices and operation of the heart. More specifically, defects such as narrowing of the valve stenosis or a defective closing of a valve, referred to as valvular insufficiency, result in accumulation of blood in a heart cavity or regurgitation of blood past the valve. If uncorrected, prolonged valvular insufficiency may cause eventually total valve replacement. On the other hand, certain diseases cause the dilation of the heat valve annulus. Dilation may also cause deformation of the valve geometry or shape displacing one or more of the valve cusps from the center of the valve. Dilation and/or deformation result in an ineffective closure of the valve during ventricular contraction, which results in regurgitation or leakage of blood during contraction.

It is known to use annuloplasty ring in the repair of diseased or damaged atrioventricular valves that do not require replacement. The annuloplasty ring is designed to support the functional changes that occur during the cardiac cycle: maintaining coaptation and valve integrity in systole while permitting good hemodynamics in diastole. The annuloplasty ring also provides support for the mitral or tricuspid annulus and restricts expansion of the annulus or portions of the annulus to preset limits. A variety of annuloplasty rings have been employed, ranging from rigid rings of fixed sizes to flexible rings with a degree of adjustability. Obviously, annular prostheses that are of rigid fixed size must be carefully selected and skillfully sutured in place. Thus, an imperfect fit may require corrective surgery to replace the improperly implanted prosthesis. A rigid ring also prevents the normal flexibility of the valve annulus and has a tendency of sutures tearing during the normal movement of the valve annulus. Examples of rigid or partially rigid annuloplasty rings are disclosed in U.S. Pat. No. 5,061,277 (to Carpentier et al.) and in U.S. Pat. No. 5,104,407 (to Lam et al.).

Over the years flexible annuloplasty rings are designed and developed to overcome the problems of rigid rings and/or fixed size. One problem associated with the fixed size annuloplasty rings of the prior art is that, when such annuloplasty rings are implanted into children, the subsequent growth of the patient may render the annuloplasty ring too small for its intended function. Thus, follow-up surgery may be necessary to replace the originally implanted annuloplasty ring with a larger ring suitable for the thencurrent size of the patient.

Carpentier et al., in U.S. Pat. No. 5,593,435 and U.S. Pat. No. 5,888,240 describes an annuloplasty ring which is constructed and equipped for post-implantation size adjustment in situ to accommodate changes in annular size due to growth of the patient. It is disclosed that a distensible annuloplasty ring may be made up of a plurality of separate segments which are slidably or movably secured to one another to form a ring. It is also disclosed that when dilatory or outward pressure is exerted against the inner surface of the ring, as may be accomplished by way of a radially expandable balloon introduced within the annulus of the remodeled valve, such pressure will cause the segments to slide or distend relative to one another. However, such mechanical sliding or distension of the segments expands the circumference of the ring by an incremental increase at only a few joint points where any two slidable segments meet. By distending an incremental strain and simultaneously loading most of the distension stress at a few joint points, the overall shape of the annulus may be distorted. Furthermore, the intended valve functionality with that unevenly distended annuloplasty ring after a period of tissue ingrowths into and/or encapsulation onto the annuloplasty ring may be compromised.

Cardiovascular stents have been developed and used widely. A stent is a generally longitudinal tubular mesh-like device formed of biocompatible material, preferably a metallic or a plastic material, which is useful in the treatment of stenosis, strictures or aneurysms in body conduits such as blood vessels or around a valvular annulus. When a stent is expanded and enlarged, the whole section is expanded at essentially the same degree of extension. Special features of the stent configuration may include radially expandable non-axial contraction and/or spirals as disclosed in U.S. Pat. No. 6,042,606 (to Frantzen) and U.S. Pat. No. 6,033,433 (to Ehr et al.).

Balloon-assisted radial expansion for an expandable annuloplasty ring might restrict the blood flow undesirably. Radial mechanical force as disclosed in the prior art to expand an annuloplasty ring at a later time might not evenly expand the ring radially. Shape-memory material has been disclosed and widely used that it will return to its preshape when it is activated by heat or other suitable means. The shape-memory material may include plastic material, metal, and the like. For example, U.S. Pat. No. 5,163,952 (to Froix), U.S. Pat. No. 5,258,020 (to Froix), and U.S. Pat. No. 5,607,467 (to Froix) all disclose shape-memory plastic while U.S. Pat. No. 6,077,298 (to Tu et al.) discloses a shape-memory metallic device. The entire contents of these patents are incorporated herein by reference.

Therefore, it would be desirable to provide a radially expandable annuloplasty ring that has uniformly distending properties circumferentially to conform to the natural growth of the valve annulus of the patient without suffering the above-discussed disadvantages of localized stress at only a few joint points where any two slidable segments meet. The improved annuloplasty ring may be preferably evenly expanded by non-mechanical means, such as shape-memory mechanisms.

SUMMARY OF THE INVENTION

In general, it is an object of the present invention to provide an expandable annuloplasty ring which may be radially expanded in situ by way of a non-mechanical expandable means. It is another object of the present invention to provide an expandable annuloplasty with essentially uniform ring distension in the circumferential direction for each expansion process. It is still another object of the present invention to provide a method for expanding the radially expandable annuloplasty by expanding means for radially expanding the annuloplasty ring to a size larger than the prior size. It is a further object of the present invention to provide expanding means including heating a shape-memory material.

In accordance with one embodiment of the invention, the annuloplasty ring may be made up of a fabric sheath, and at least one stenting element mounted within the fabric sheath, wherein the at least one stenting element is made of shape-memory material. The shape-memory material has a preshape and a shape-transition temperature, wherein the shape-memory material expands to its preshape so as to expand the annuloplasty ring when the shape-memory material is heated to above the shape-transition temperature. In one embodiment, the annuloplasty ring so formed is a completely close ring while in an alternative embodiment, the annuloplasty ring is an open ring. The annuloplasty ring has the desired configuration of the mitral or tricuspid valve annulus. In one preferred embodiment, the shape-memory material is selected from a group consisting of shape-memory Nitinol, shape-memory plastic, or the like.

The shape-memory material may be embedded within a biocompatible substrate selected from a group consisting of silicone, polyurethane, expanded polytetrafluoroethylene, semi-permeable material, elastomer, mixture of said biocompatible substrate thereof, and the like. The embedding may make the annoloplasty ring impermeable to blood and provide supportive strength. Furthermore, an internal space of the fabric sheath may comprise a therapeutic agent selected from a group consisting of heparin agent, virucidal agent, anti-ulcer agent, anti-inflammatory agent, antibiotics, anti-cancer agent, and mixture of said therapeutic agent thereof.

In another preferred embodiment, the shape-transition temperature for the shapememory material is preferably between about 39° C. and about 90° C. The shape-transition temperature is further preferred at a temperature region that is sufficient to cause the shape-memory material to transform to its preshape but not too high to undesirably affect the tissues. The source of heat for heating the shape-memory material to above the shape-transition temperature may be selected from a group consisting of radiofrequency energy, heated balloon, infrared energy, ultrasound energy, and laser energy. Alternately, the source of heat may comprise an external magnetic circuit or other remote source.

The fabric sheath may be stretchable or distensible to accommodate the distension of the annuloplasty ring at a later time. In a further embodiment, the fabric sheath may be impermeable to prevent blood from entering into the inner spaces. It may also comprise a silicone layer so that the annuloplasty ring is substantially impermeable to blood or blood components. The silicone layer may be placed between the fabric sheath and the inner circular members of the annular ring. The fabric sheath may be suturable to facilitate suturing-in-place of the ring to the surrounding anatomical tissue. The fabric sheath may be made of Dacron or other biocompatible material.

In accordance with another embodiment of the invention, the expandable annuloplasty ring for implantation in a heart valve annulus may comprise a fabric sheath and a plurality of stenting elements mounted within the fabric sheath, wherein each of the plurality of stenting elements is made of shape-memory material having a preshape and its own shape-transition temperature, wherein each shape-memory material expands to its preshape when that shape-memory material is heated to above its own shape-transition temperature.

In still another embodiment, there is provided a method for radially expanding an expandable annuloplasty ring implanted in an annulus of a heart valve of a patient. The method may comprise the steps of implanting within the annulus an expandable annuloplasty ring having a fabric sheath and at least one stenting element mounted within the fabric sheath, wherein the at least one stenting element is made of shape-memory material. Subsequently, after predetermined time duration, apply heat for radially expanding the annuloplasty ring to a size larger than the size at implantation, wherein the shape-memory material expands to its preshape when the shape-memory material is heated to above the shape-transition temperature.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

With reference to the drawings FIGS. 1 to 4, what is shown is an embodiment of an expandable annuloplasty ring made of shape-memory material having essentially uniform distensibility in the circumferential direction of the ring.

Figure 1:
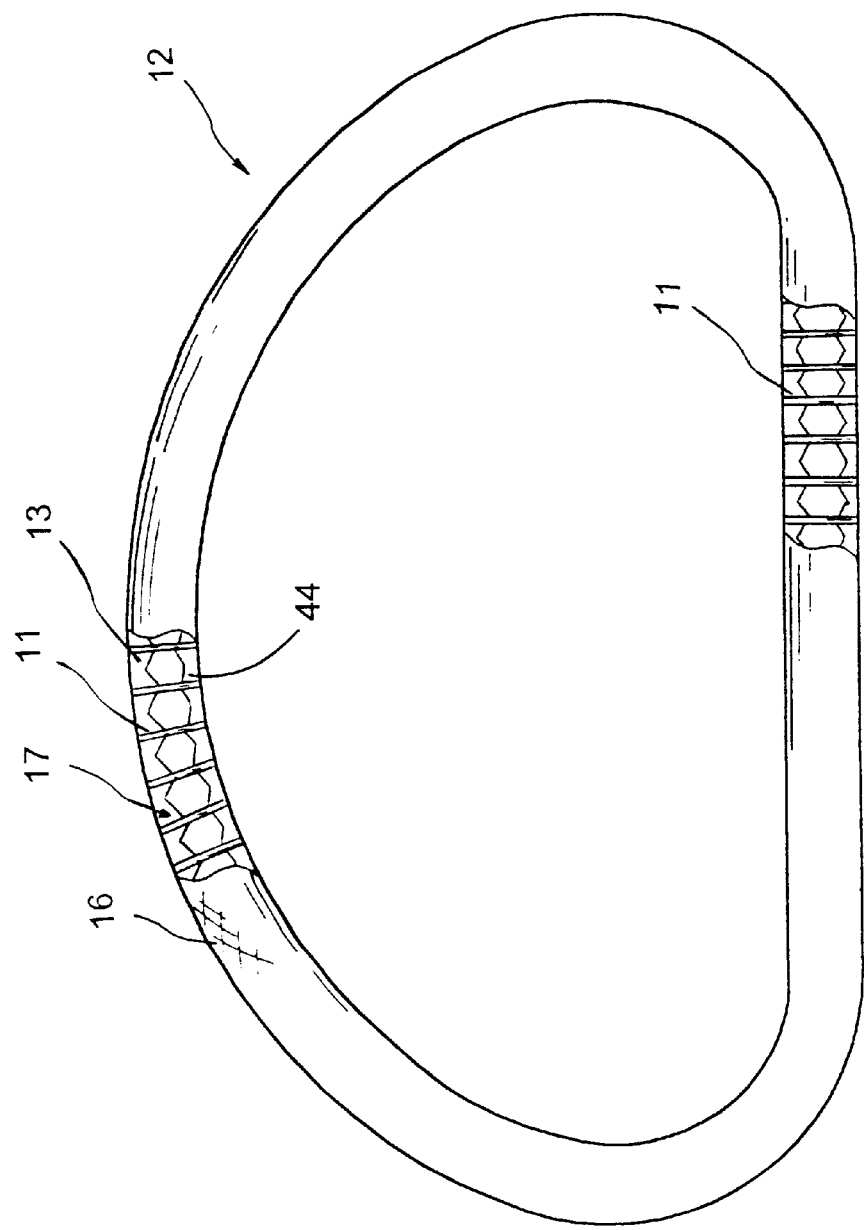
FIG. 1 is a partial perspective view of an embodiment of the expandable annuloplasty ring of the present invention.

FIG. 1 shows a partial perspective view of a first embodiment of the expandable annuloplasty ring of the present invention. The annuloplasty ring 12 comprises a fabric sheath 16 and an annular ring 17. In one embodiment, the annular ring 17 comprises a plurality of circular members 11 mounted within the fabric sheath 16 and spaced from one another, wherein each of the plurality of circular members 11 is securely joined to an adjacent circular member by at least one stenting element 13 (and/or 44) so as to form a continuous annular ring, wherein the at least one stenting element is made of shape-memory material. The shape-memory material may be selected from a group consisting of shape-memory Nitinol, shape-memory plastic, or other shape-memory substrate. The shape-memory material has a preshape and a shape-transition temperature, wherein the shape-memory material may be manipulated or constrained at will before an expansion state but expand to its preshape so as to expand circumferentially the annuloplasty ring when the shape-memory material is heated to above the associated shape-transition temperature.

For drug therapeutics purposes, the internal space within the annulus ring or inside the fabric sheath may contain a therapeutic agent selected from a group consisting of heparin agent, virucidal agent, anti-ulcer agent, anti-inflammatory agent, antibiotics, anti-cancer agent, and mixture of said therapeutic agent thereof.

The plurality of circular members 11 may be selected from the group consisting of Nitinol, Nickel-Titanium alloy, stainless steel, biocompatible metal, biocompatible plastic, and the like. The shape of the at least one of the plurality of circular members may be selected from the group consisting of a round shape, an oval shape, a C-shape, a D-shape, a U-shape, an open circular shape, and an irregular shape. The circular member may be relatively rigid or semi-flexible so as to support the valvular annulus during the heart valve functions of opening and closing.

The stenting elements 13, 44 are generally rigid and non-axially contractible so as to maintain the circumferential distance and the general shape of the annuloplasty ring. The stenting element may be distended axially (that is, in a circumferential direction when the stenting element is considered as a part of the whole annular ring) by force or by returning to its preshape and stays at the distended state upon distending. Frantzen in U.S. Pat. No. 6,042,606 discloses a radially expandable non-axially contracting surgical stent. By incorporating an extra tie-bar between any two wave-like struts of a conventional stent, axial contraction of the stent is avoided when the stent is radially expanded. The stenting element of the present invention may comprise a plurality of struts with tie-bars so as to maintain the circumferential integrity of the annular ring. U.S. Pat. No. 6,042,606 is incorporated herein by reference.

The circular members and their coupled stenting elements constitute the annular ring. As disclosed in a patent pending Ser. No. 09/587,135, when dilatory or outward pressure is exerted against the inner surface of the annular ring introduced within the annulus, the stenting element may distend circumferentially while the annular ring expands radially. The stenting element may be selected from the group consisting of a mesh, a zigzag wire, a spiral wire, a stretchable stent, a spiral-like structure, and the like. In a preferred embodiment, the shape-memory stenting element is constrained or compressed in the original annuloplasty ring fabrication. It may be dissented to its preshape by heating the stenting element above its shape-transition temperature.

Ehr et al. in U.S. Pat. No. 6,033,433 discloses a stent having spiral structures between expandable segments which absorbs excess stress when the expandable segments are expanded so as to avoid stent recoiling. The stenting element of the present invention may comprise a spiral structure or spiral wire to relieve the undesired local stress upon radial expansion of the annuloplasty ring. U.S. Pat. No. 6,033,433 is also incorporated herein by reference.

Figure 2A:
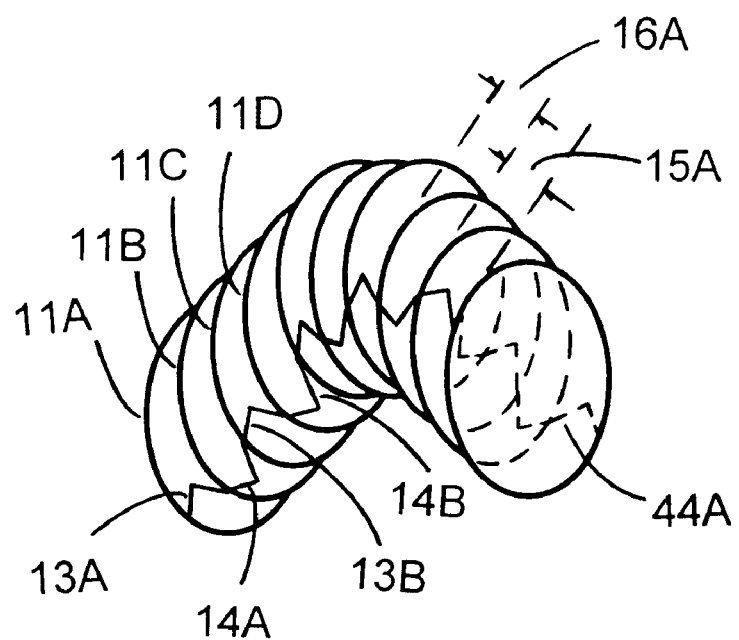
FIG. 2A is a perspective view of a plurality of stenting elements made of shape-memory material for the annuloplasty ring at a pre-expansion state.

FIG. 2A shows a perspective view of the plurality of circular members 11A, 11B, 11C, 11D and a plurality of stenting elements 13A, 13B, 14A, 14B made of shape-memory material at a pre-expansion state. For illustration purposes, at a pre-expansion state, a circular member 11A is securely joined to an adjacent circular member 11B by at least a stenting element 13A. Similarly, a circular member 11C is securely joined to an adjacent circular member 11D by at least another stenting element 14A. In one preferred embodiment, the first group of stenting elements 13A, 13B is made of shape-memory material having a first shape-transition temperature which is different from that for the second group of stenting elements 14A, 14B, which have a second shape-transition temperature. The stenting elements of the present invention may comprise a plurality of groups, all having different shape-transition temperatures. Alternatively, at least one additional stenting element 44A may be used to securely join any two circular members at a location away from the prior joint point of a prior stenting element. The at least one additional stenting element, such as 44A may have the same or different shape-transition temperature as the corresponding stenting element for those two circular members.

The space or distance 15A between any two adjacent circular members and bridged by at least one stenting element 13A, or 13B of the first group of shape-memory material may be distended axially at above the first shape-transition temperature of that material. In an additional embodiment, the space or distance 16A between any two adjacent circular members and bridged by at least one stenting element 14A, or 14B of the second group of shape-memory material may be distended axially at above the second shape-transition temperature associated with the second group of shape-memory material.

Figure 2B:
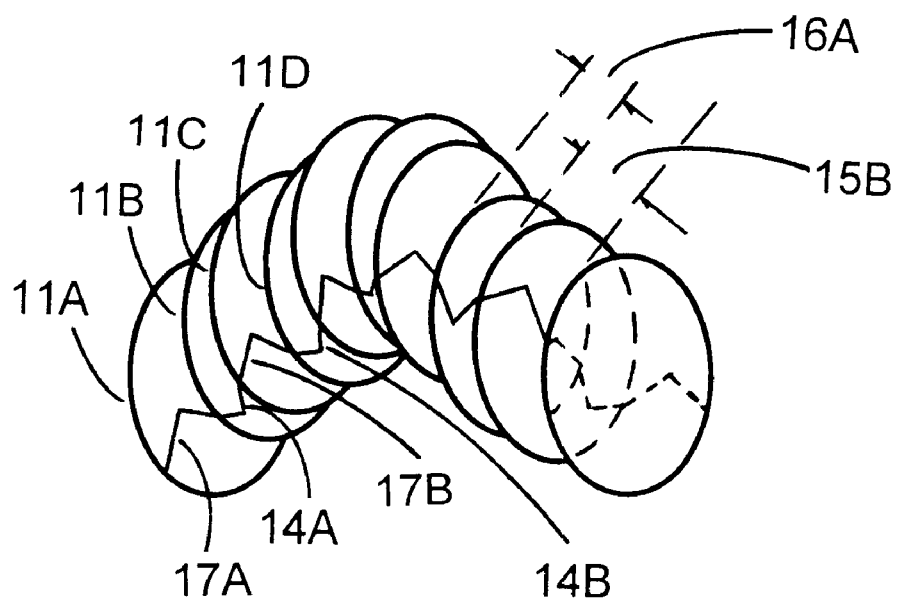
FIG. 2B is a perspective view of the corresponding plurality of stenting elements of FIG. 2A at a first post-expansion state.

FIG. 2B shows a perspective view of the corresponding plurality of stenting elements of FIG. 2A at a first post-expansion state by heating the stenting element above its first shape-transition temperature. The distended stenting elements 17A distended from 13A (and/or 17B via 13B) as shown in FIG. 2B increase the distance between the two adjacent circular members of the first group shape-memory material from 15A to 15B. At this first post-expansion state, the stenting elements 14A, 14B made of the second group shape-memory material do not distend because the activating temperature is still below the second shape-transition temperature.

Figure 2C:
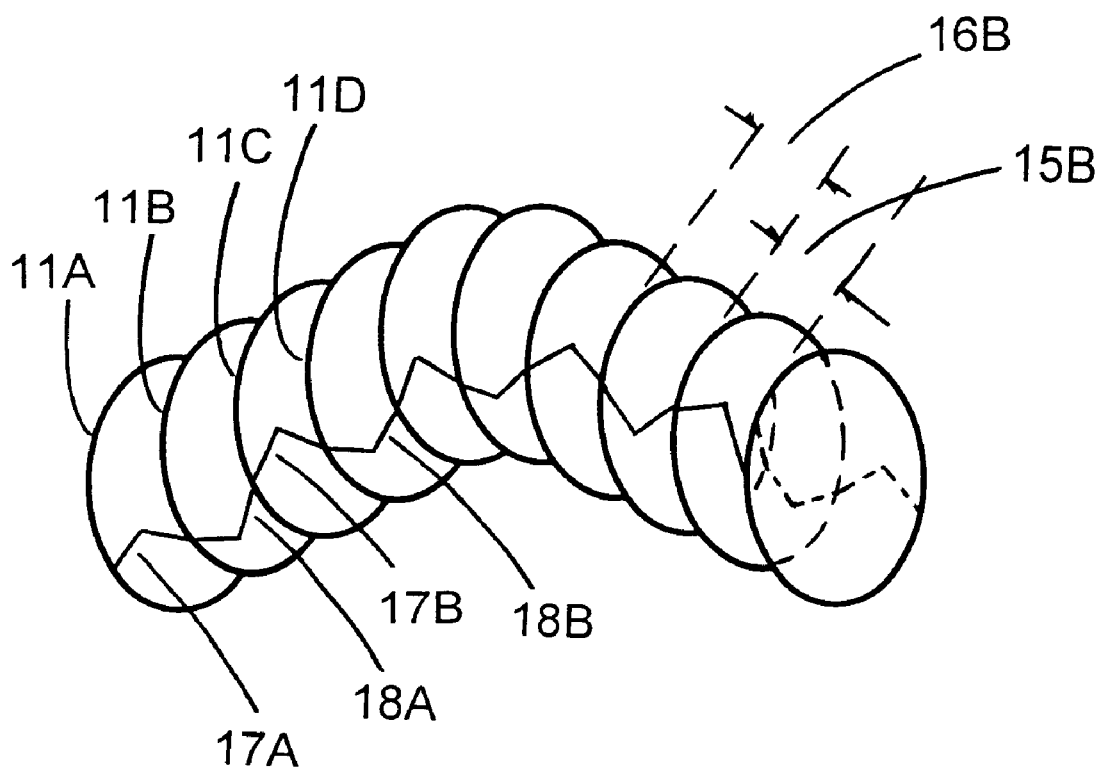
FIG. 2C is a perspective view of the corresponding plurality of stenting elements of FIG. 2A at a second post-expansion state.

FIG. 2C shows a perspective view of the corresponding plurality of stenting elements of FIG. 2A at a second post-expansion state by heating the stenting element above its second shape-transition temperature that is higher than the first shape-transition temperature. The distended stenting elements 18A distended from 14A (and/or 18B via 14B) as shown in FIG. 2C increase the distance between the two adjacent circular members of the second group shape-memory material from 16A to 16B. At this second post-expansion state, the stenting elements 17A, 17B made of the first group shape-memory material do not distend any further because they are already at their preshape.

Figure 3B:
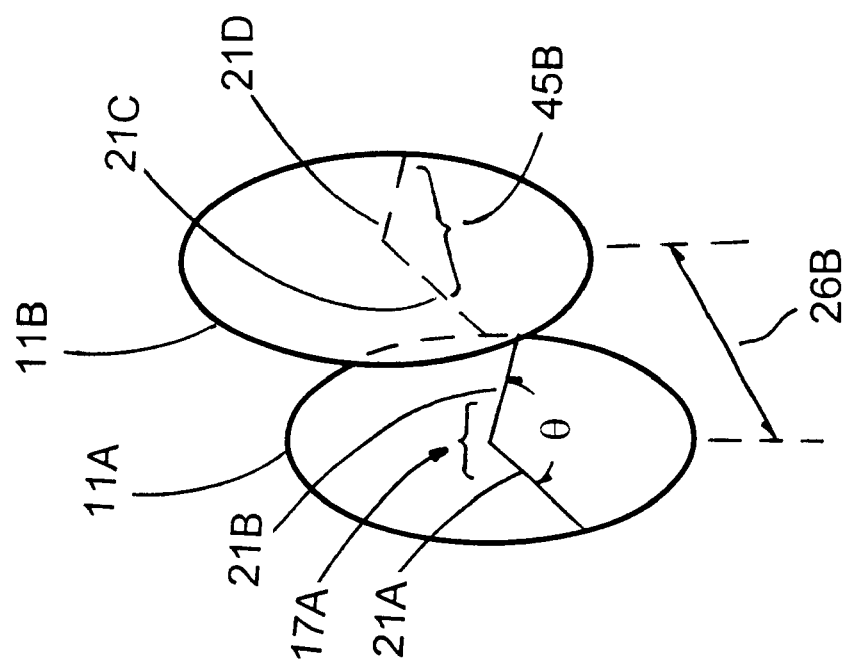
FIG. 3B is a schematic diagram illustrating one embodiment of the mechanisms for expanding the stenting elements made of memory-shape material axially outwardly at a post-expansion state leading to circumferential expansion of an annuloplasty ring.
Figure 3A:
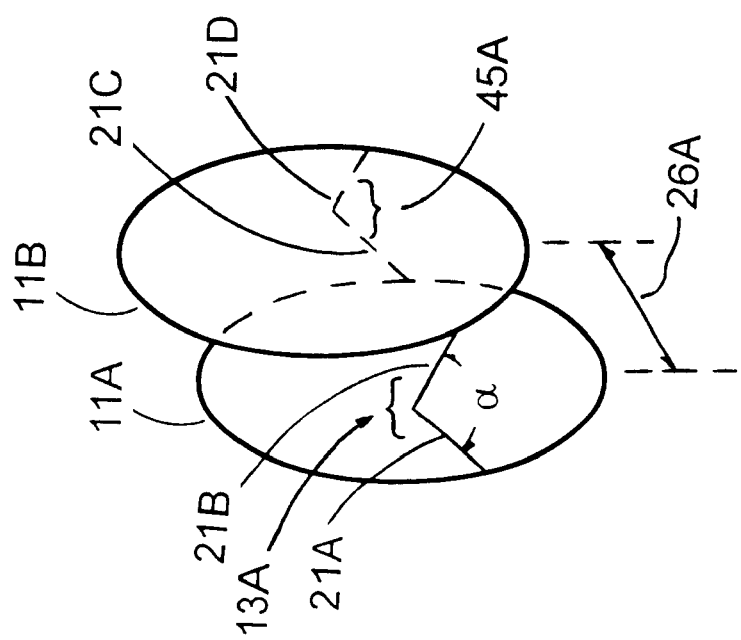
FIG. 3A is a schematic diagram illustrating one embodiment of the mechanisms for expanding the stenting elements made of memory-shape material axially outwardly at a pre-expansion state.

FIG. 3A and FIG. 3B show schematic diagrams illustrating one embodiment of the mechanisms for expanding the stenting element 13A made of memory-shape material axially outwardly leading to circumferential expansion of an annuloplasty ring. The two adjacent circular rings 11A, 11B may be essentially parallel to each other. The distance between these two adjacent circular members 11A, 11B at a pre-expansion state is designated as 26A, while the two circular members may be joined by one stenting element 13A or at least one more stenting element 45A. In one illustrative embodiment, the stenting element 13A comprises two joint bars 21A and 21B that have been constrained at an angle $\alpha$ at a pre-expansion state. Similarly, the stenting element 45A comprises two joint bars 21C and 21D that have been constrained at a pre-expansion state. The purpose of the stenting elements is to support the circular member 11A, 11B in essentially perpendicular to a circumferential reference line of the annular ring. Another purpose of the stenting elements is to maintain the distance between the two adjacent circular members either at a pre-expansion state (that is, pre-distending state), or at a post-expansion state (that is, post-distending state).

Upon one expansion process by applying the expanding means of the present invention at a temperature above its first shape-transition temperature, the stenting elements 13A, 45A may be distended/stretched to be as 17A and 45B, respectively as shown in FIG. 3B. The distance between the two adjacent circular members 11A and 11B may increase from 26A to 26B after a first expansion and maintain the distended distance. At a first expansion state, the stenting element 17A comprising two joint bars 21A and 21B becomes conformed to its preshape at an angle $\theta$. Upon an optional second expansion process at a temperature above the second shape-transition temperature, the stenting elements made of second group shape-memory material may distend to their preshape. Therefore, it is understandable that the total circumference of the annular ring may be adjusted more than once when there is more than one group of shape-memory stenting elements. The distending process and mechanism for maintaining a stent-like structure at the distended state as applied to the stenting element of the present invention is well known to one artisan who is skilled in the art.

Figure 4:
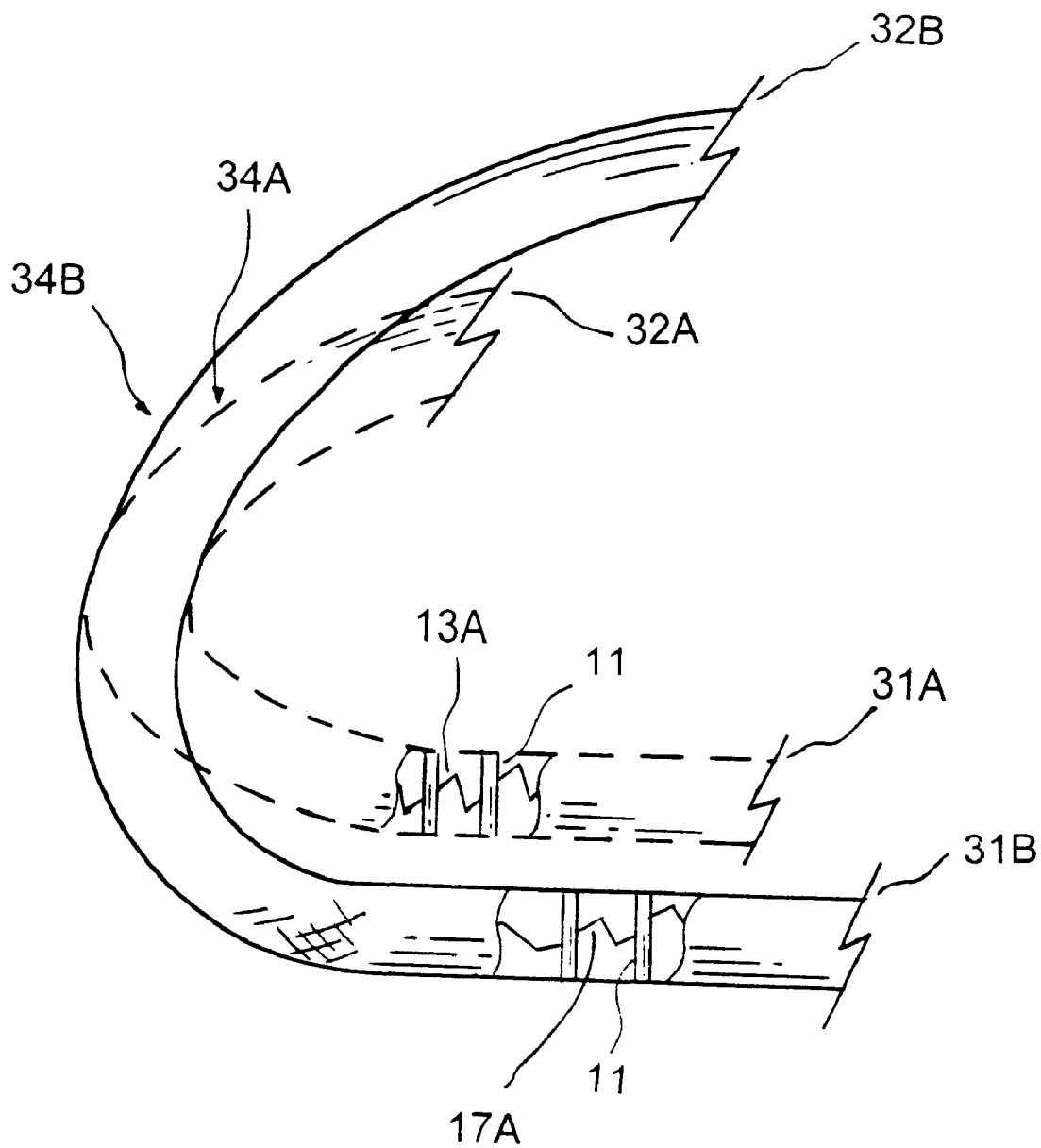
FIG. 4 is a cut-away illustration of an annuloplasty ring before and after circumferential expansion.

FIG. 4 shows a cut-away illustration of an annuloplasty ring before and after a radial expansion, that is, circumferential stretching. A first reference point 31A of a pre-expansion annuloplasty ring 34A becomes the reference point 31B for a first post-expansion annuloplasty ring 34B. A second reference point 32A from a pre-expansion annuloplasty ring 34A becomes the second reference point 32B for a first post-expansion annuloplasty ring 34B. Similarly, one of the at least one stenting element 13A between two adjacent circular rings 11 has been extended to become 17A at a post-expansion state.

One method by which the size of the annuloplasty ring may be expanded is through introduction of heating to heat the shape-memory stenting element to above its shape-transition temperature so as to convert the constrained configuration to its preshape configuration. The source of heat may be selected from a group consisting of radiofrequency (RF) energy, heated balloon, infrared (IR) energy, ultrasound energy, and laser energy. The heat is generally introduced to the stenting element through a catheter, a wire, a conducting wire, fiber optics, or other appropriate means. In one embodiment of the present invention, the stenting elements may be electrically connected to each other so as to transfer the heat or energy through all or part of the stenting elements of the annular ring.

In an alternate embodiment, the source of heat may comprise an external magnetic circuit, whereby heating of the shape-memory stenting element is induced based when placed into an alternative magnetic field. Accordingly, magnetic flux rapid alteration results in power loss to the magnetic circuit that appears as heat on the stenting element in vivo. Other non-invasive methods for heating the shape-memory stenting elements of the present invention may be applied and covered in the disclosure.

In an illustrative embodiment, a method for radially expanding an expandable annuloplasty ring implanted in an annulus of a heart valve of a patient, the method comprising steps of implanting within the annulus an expandable annuloplasty ring having a fabric sheath and at least one stenting element mounted within said fabric sheath, wherein said at least one stenting element is made of shape-memory material, the shape-memory material having a preshape and a shape-transition temperature And subsequently, after a predetermined time duration, applying heat for radially expanding the annuloplasty ring to a size larger than the size at implantation, wherein the shape-memory material expands to its preshape when said shape-memory material is heated to above the shape-transition temperature.

From the foregoing description, it should now be appreciated that a radially expandable annuloplasty ring having essentially uniform ring distension in the circumferential direction has been disclosed for implantation in a heart valve annulus. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. An expandable annuloplasty ring for implantation in a heart valve annulus configured for essentially uniform ring distension in a circumferential direction after an expansion process comprising a fabric sheath; and a plurality of stenting elements mounted within said fabric sheath configured to form a ring, wherein a first of the plurality of stenting elements is made of a first shape-memory material having a preshape and a first shape-transition temperature, wherein the first shape-memory material expands to its preshape when said first shape-memory material is heated to above the first shape-transition temperature, wherein the plurality of stenting elements further comprises a second stenting element made of a second shape-memory material having a preshape and a second shape-transition temperature, wherein the second shape-memory material expands to its preshape when said second shape-memory material is heated to above the second shape-transition temperature.

2. The expandable annuloplasty ring according to claim 1, wherein the plurality of stenting elements further comprises a third stenting element made of a third shape-memory material having a preshape and a third shape-transition temperature, wherein the third shape-memory material expands to its preshape when said third shape-memory material is heated to above the third shape-transition temperature.

3. The expandable annuloplasty ring according to claim 1, wherein said fabric sheath is a distensible sheath.

4. The expandable annuloplasty ring according to claim 1, wherein said shape-memory material is selected from a group consisting of shape-memory Nitinol and shape-memory plastic.

5. The expandable annuloplasty ring according to claim 1, wherein said shape-memory material is embedded within a biocompatible substrate selected from a group consisting of silicone, polyurethane, expanded polytetrafluoroethylene, semi-permeable material, elastomer and mixture of said biocompatible substrate thereof.

6. A method for radially expanding an expandable annuloplasty ring implanted in an annulus of a heart valve of a patient, the method comprising steps of: implanting within the annulus an expandable annuloplasty ring configured for essentially uniform ring distension in a circumferential direction after an expansion process having a fabric sheath and a plurality of stenting elements mounted within said fabric sheath configured to form a ring, wherein said at least one stenting element is made of shape-memory material, the shape-memory material having a preshape and a shape-transition temperature; after a predetermined time duration, applying heat for radially expanding the annuloplasty ring to a size larger than the size at implantation, wherein the shape-memory material expands to its preshape when said shape-memory material is heated to above the shape-transition temperature, wherein the expandable annuloplasty ring further comprises a second stenting element made of shape-memory material, the second stenting element having a preshape and a second shape-transition temperature, the method further comprising applying heat for radially expanding the annuloplasty ring to a size larger than the size at first expansion, wherein the second stenting element expands to its preshape when said second stenting element is heated to above the second shape-transition temperature.

* * * * *